(12) United States Patent
Brandt

(10) Patent No.: US 11,610,669 B2
(45) Date of Patent: Mar. 21, 2023

(54) METHOD AND SYSTEM FOR ASSEMBLING SETS OF MEDICAL INSTRUMENTS AND/OR PHARMACEUTICAL PRODUCTS

(71) Applicant: CONSAT ENGINEERING AB, Partille (SE)

(72) Inventor: Emil Brandt, Alingsås (SE)

(73) Assignee: CONSAT ENGINEERING AB, Partille (SE)

( * ) Notice: Subject to any disclaimer, the term of this patent is extended or adjusted under 35 U.S.C. 154(b) by 636 days.

(21) Appl. No.: 16/612,113

(22) PCT Filed: May 14, 2018

(86) PCT No.: PCT/EP2018/062359
§ 371 (c)(1),
(2) Date: Nov. 8, 2019

(87) PCT Pub. No.: WO2018/210742
PCT Pub. Date: Nov. 22, 2018

(65) Prior Publication Data
US 2020/0168322 A1 May 28, 2020

(30) Foreign Application Priority Data
May 15, 2017 (EP) .................................... 17170978

(51) Int. Cl.
*G16H 40/20* (2018.01)
*A61J 3/06* (2006.01)
*G16H 20/10* (2018.01)

(52) U.S. Cl.
CPC ............... *G16H 40/20* (2018.01); *A61J 3/06* (2013.01); *G16H 20/10* (2018.01);
(Continued)

(58) Field of Classification Search
CPC .. G16H 40/20; G16H 20/10; A61J 3/06; A61J 2205/30; A61J 2200/74; A61J 2205/60; A61J 2205/10
See application file for complete search history.

(56) References Cited

U.S. PATENT DOCUMENTS 5,905,653 A * 5/1999 Higham ............... G07F 17/0092
700/242
6,339,732 B1 * 1/2002 Phoon ................... A61J 7/0084
700/237
(Continued)

FOREIGN PATENT DOCUMENTS

DE 102005007730 A1 * 8/2006 ........... G06F 19/322
DE 102005007730 A1 8/2006
(Continued)

OTHER PUBLICATIONS

Extended European Search Report dated Nov. 8, 2017, issued by the European Patent Office in corresponding European Application No. 17170978.5-1659, (6 pages).
(Continued)

*Primary Examiner* — Michael Collins
(74) *Attorney, Agent, or Firm* — Buchanan Ingersoll & Rooney P.C.

(57) ABSTRACT

A method and system for assembling sets of medical instruments and/or pharmaceutical products. The system includes a control system comprising or being connected to a database comprising data objects corresponding to available objects. An input area is provided to receive batches of unsorted medical instruments or pharmaceutical product containers, and an identification area having an identification unit. A temporary sorting area is also provided, including a plurality of storage positions provided with visual indications capable of visually indicating one of the storage position at a time, and an output area, possibly being
(Continued)

overlapping with the input area, arranged to receive medical instruments and/or pharmaceutical products as assembled sets. The controller is arranged to receive information from the identification unit obtained when an item is arranged on the identification area, and to identify the item in the database.

15 Claims, 12 Drawing Sheets

(52) U.S. Cl.
CPC ........ *A61J 2200/74* (2013.01); *A61J 2205/10* (2013.01); *A61J 2205/30* (2013.01); *A61J 2205/60* (2013.01)

(56) References Cited

U.S. PATENT DOCUMENTS

| | | | |
|---|---|---|---|
| 7,426,425 B2 * | 9/2008 | Meek, Jr. | G06Q 10/087 700/242 |
| 8,554,365 B2 * | 10/2013 | Thomas | G07G 1/01 700/242 |
| 8,753,059 B2 | 6/2014 | Baker | |
| 9,259,844 B2 | 2/2016 | Xu et al. | |
| 9,367,984 B2 * | 6/2016 | Daugbjerg | E05B 65/46 |
| 9,427,520 B2 * | 8/2016 | Batch | G16H 40/67 |
| 11,328,802 B2 * | 5/2022 | Waterson | G06Q 10/10 |
| 2005/0038556 A1 | 2/2005 | Gagnon et al. | |
| 2007/0001839 A1 | 1/2007 | Cambre et al. | |
| 2009/0137882 A1 * | 5/2009 | Baudino | G16H 50/80 600/300 |
| 2013/0164103 A1 | 6/2013 | Baker | |
| 2016/0042130 A1 | 2/2016 | Broninx | |
| 2017/0061375 A1 * | 3/2017 | Laster | G16H 10/60 |
| 2020/0273560 A1 * | 8/2020 | Wolf | G06F 16/71 |

FOREIGN PATENT DOCUMENTS

| | | |
|---|---|---|
| WO | 2017011646 A1 | 1/2017 |
| WO | WO-2017011646 A1 * | 1/2017 |

OTHER PUBLICATIONS

International Search Report (PCT/ISA/210) and Written Opinion (PCT/ISA/237) dated Jun. 22, 2018, by the European Patent Office as the International Searching Authority for International Application No. PCT/EP2018/062359.

Office Action (Communication pursuant to Article 94(3) EPC) dated Nov. 19, 2021, issued by the European Patent Office in corresponding European Application No. 17 170 978.5-1113, (6 pages).

* cited by examiner

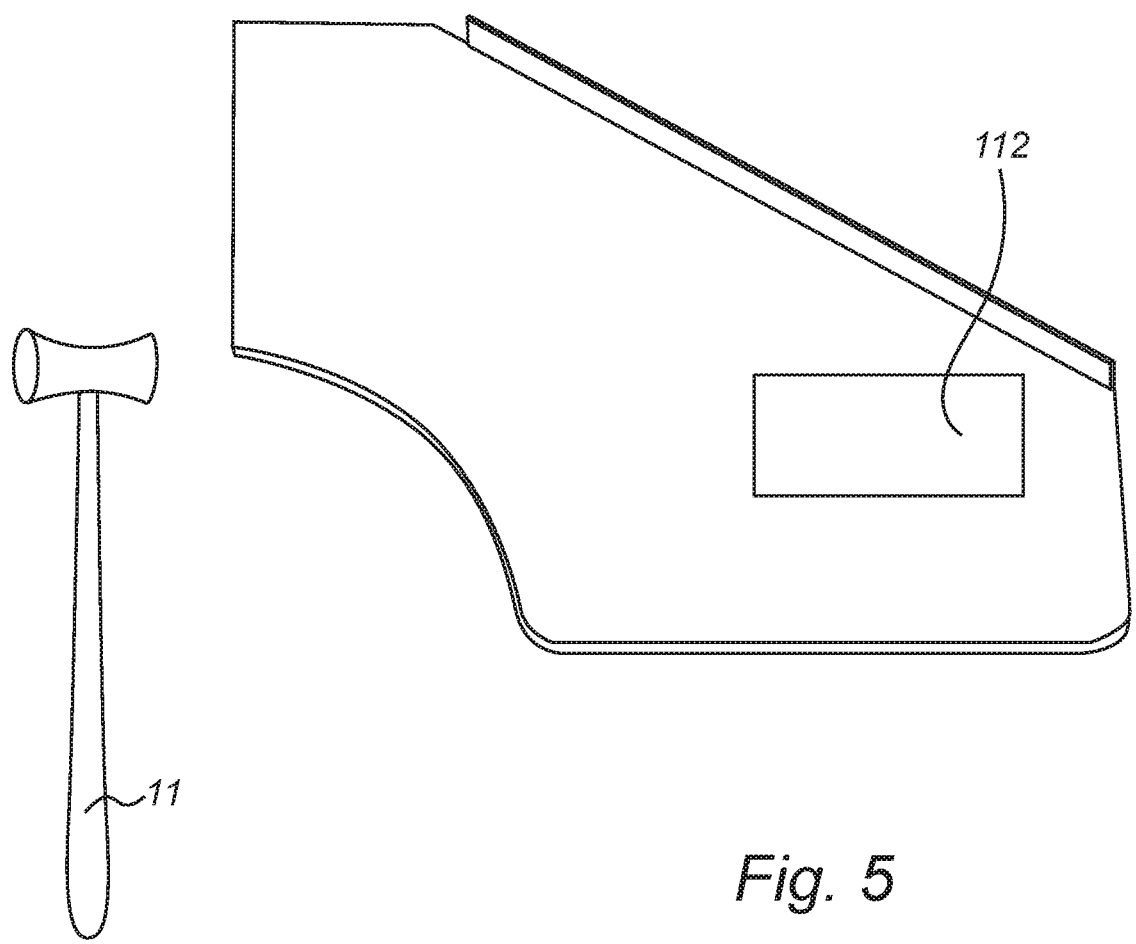
Fig. 5
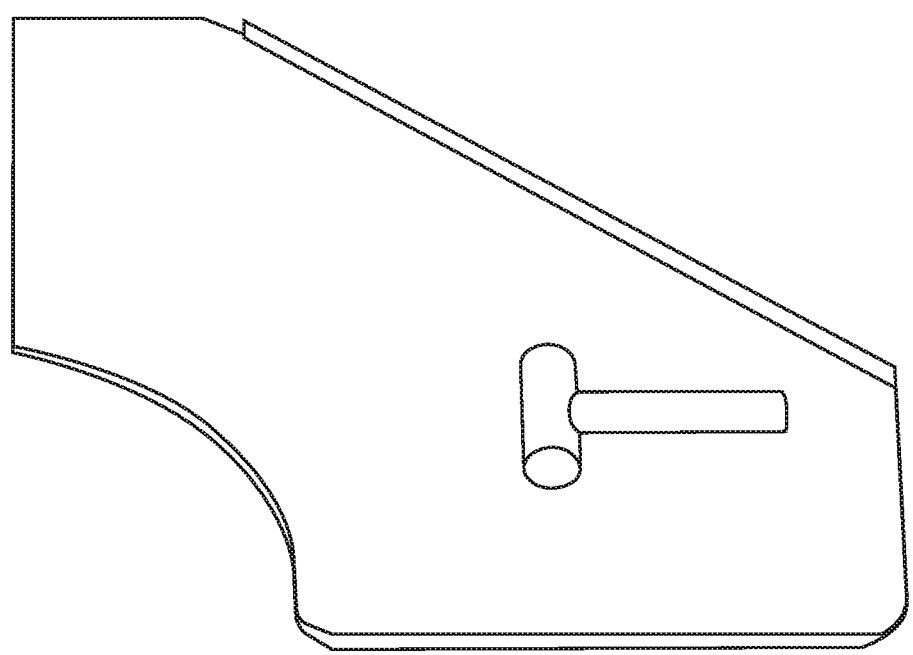

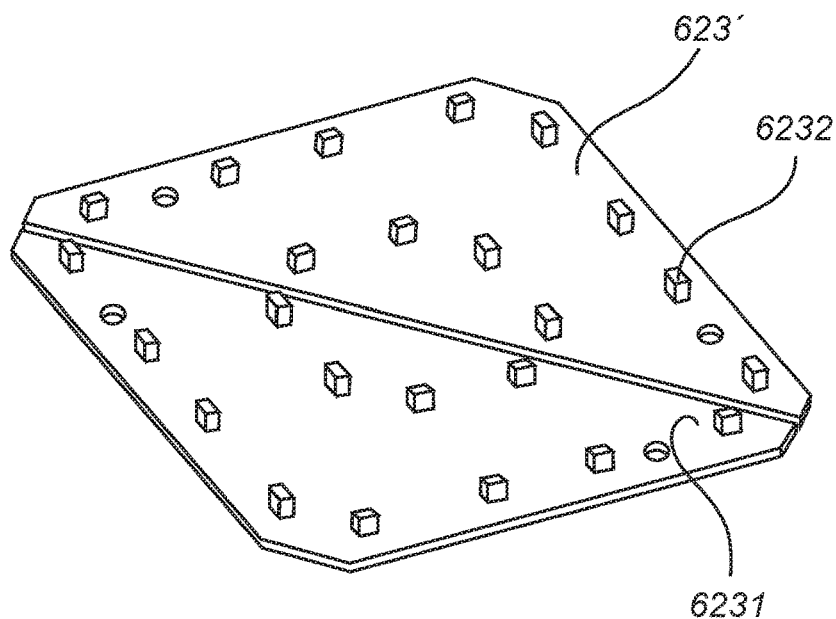
*Fig. 6*
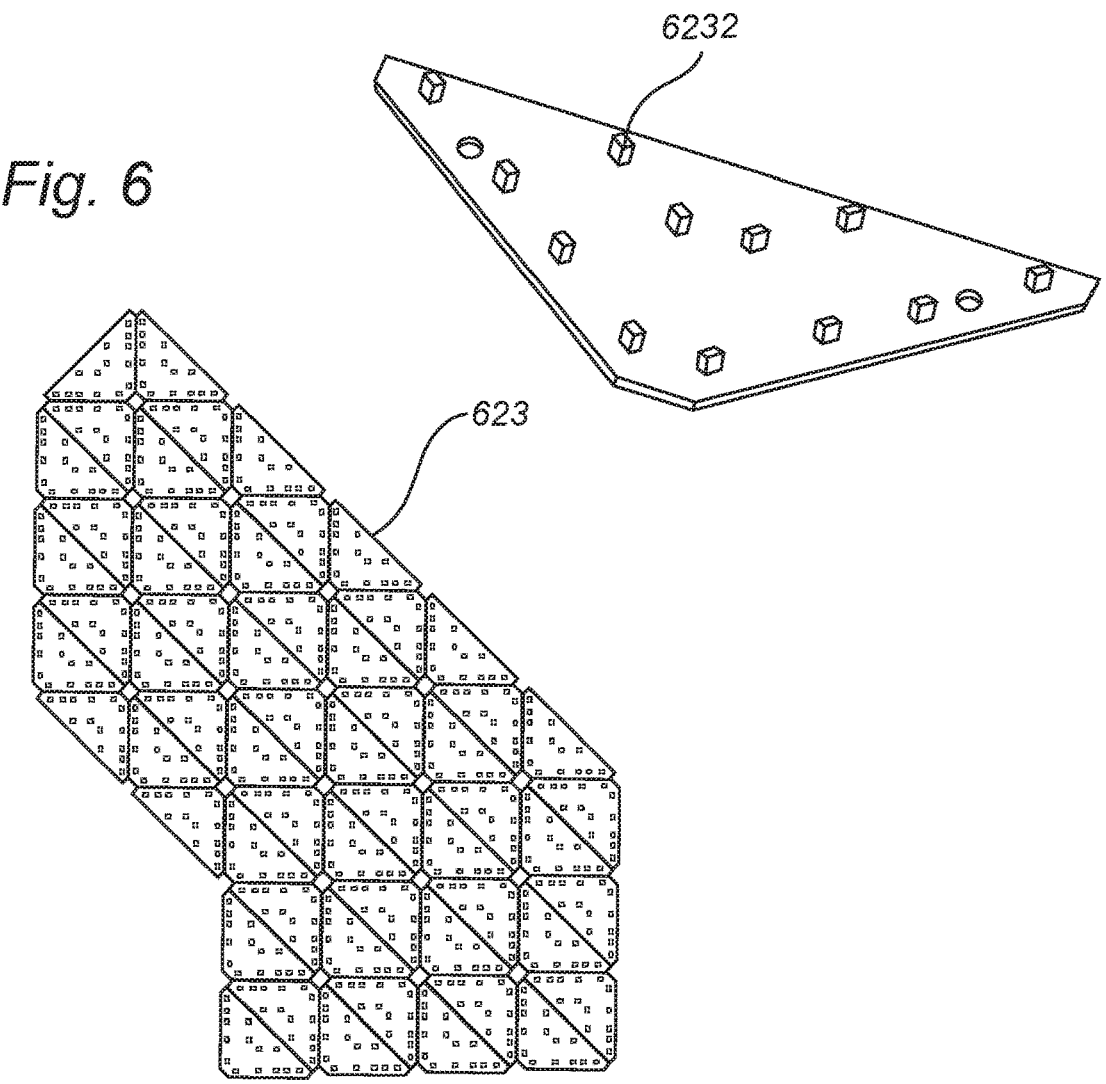

METHOD AND SYSTEM FOR ASSEMBLING SETS OF MEDICAL INSTRUMENTS AND/OR PHARMACEUTICAL PRODUCTS

TECHNICAL FIELD OF THE INVENTION

The present invention relates to a method and a system for assembling sets of medical instruments and/or pharmaceutical products.

BACKGROUND

In hospitals, thousands of medical instruments are used during surgical operations and the like every day. Most of these instruments are reusable, and after the tools have been used they need to be cleaned and later sterilized. Before sterilization, the tools need to be manually checked for quality defects, sorted and assembled in a suitable container, such as a metal tray. The process of assembling, sterilizing, transporting and storing the tools, all in a sterile state, is complex. The assembling typically takes place in a separate room, normally a clean room, and normally arranged between a cleaning area and a sterilization area, either arranged in hospitals or the like, or in external cleaning centers.

This assembling process is today predominantly performed manually, with very limited technical assistance. Thus, the quality of the assembling is dependent on the training and experience of the persons doing the work, and a very long training period under adequate supervision is today required before an operator is able to perform the work independently. In Sweden, the education to be allowed to perform this work is 1.5 years at a vocational university and then between one and two years of training together with a supervisor. Alternatively, highly experienced auxiliary nurses can do the same training and then be able to perform the work, but still requiring a similar amount of training under supervision.

Due to a large variation of different tools this process is complex and time consuming. Also, many tools look very similar to each other, and it is therefore difficult to distinguish between them. This is one of the reasons why a long prior training is needed. Furthermore, the work is carried out in different ways depending on the experience of the operator, leading to difficulties when trying to ensure that the work is performed in an efficient way.

Typically, a large hospital has at its disposition thousands of reusable medical instruments, and often tens of thousands. An assembled set may comprise hundreds of instruments, but a typical size is 25-50 instruments. About 50% of the instruments are typically different forceps and scissors, which are often similar to each other and difficult to discern from each other.

The manual process is very cumbersome and costly, and often lacks in quality. If there is a mistake made in the assembling process, there is no possibility to discover this until just before the operation is to take place, when the nurses do the preparation. This means that it is very important that the process is correctly performed and that no mistakes are made.

There is therefore a need to make this assembling process more accurate and efficient, with lower lead time, and to lower the demands on training and experience for the operators.

Some attempts have been made to make the assembling process fully automated. For example, U.S. Pat. No. 8,753,059, US 2016/0042130, U.S. Pat. No. 9,259,844 and US 2005/0038556 discloses such automated systems. However, these systems are very expensive to install and use, and are also large, making it difficult to integrate these systems in existing facilities.

Similar difficulties and problems are present in many other medically related situations. For example, there is often a requirement to reassemble tools in accordance with a sorting/assembling list immediately after a surgical procedure, to ensure that all instruments are sent back, and to make sure that no instruments from the original set is missing, and in the worst case remains inside a patient.

A similar problem is found for distribution of drugs in hospitals and the like. A trained nurse will generally assemble the prescribed set of different drugs for a number of patients at a time. The drugs are assembled to sets corresponding to a certain patient and a certain time. This work is today typically made manually, with no technical assistance, and requires extensive care and training, since errors may have fatal consequences.

There is therefore a need for an improved method and system for assembling sets of medical instruments and/or pharmaceutical products, which makes the assembling more efficient and reduces the risk of errors.

SUMMARY OF THE INVENTION

It is therefore an object of the present invention to provide a method and system for assembling sets of medical instruments and/or pharmaceutical products which alleviate all or at least some of the above-discussed drawbacks of the presently known systems.

This object is achieved by means of a method and system as defined in the appended claims.

According to a first aspect of the invention, there is provided a system for assembling sets of medical instruments and/or pharmaceutical products, the system comprising:

a control system comprising or being connected to a database, said database comprising data objects corresponding to available medical instruments and/or pharmaceutical products;

an input area, arranged to receive batches of unsorted medical instruments or pharmaceutical product containers;

an identification area having an identification unit;

a temporary sorting area comprising a plurality of storage positions for medical instruments and/or pharmaceutical product containers, the storage positions being provided with visual indications capable of visually indicating one of said plurality of storage position at a time; and an output area, possibly being overlapping with the input area, arranged to receive medical instruments and/or pharmaceutical products as assembled sets;

wherein the controller is arranged to receive information from the identification unit obtained when a medical instrument and/or pharmaceutical product container is arranged on said identification area, and to identify the medical instruments or pharmaceutical product container in said database, to dedicate and visually indicate an empty storage position for said identified medical instrument or pharmaceutical product container in said temporary sorting area and to visually indicate occupied storage positions in said temporary sorting area one at a time in accordance with a set order.

Medical instrument here relates to any type of tools and instruments used in medical procedures, such as in surgical procedures. In particular, the invention is concerned with medical instruments which are reusable, and which after use are cleaned and sterilized for further use.

Pharmaceutical product relates to drugs in any form. In particular, the invention is concerned with pharmaceutical products in administration doses, and in particular pharmaceuticals in solid form, and most particularly in the form of pills.

With the assembly system of the present invention, assembling becomes easier, quicker and more accurate. The assembling process is hereby also easily logged and verified, thereby increasing security, since the risk of errors is minimized, and any few errors happening could easily be traced and analyzed. Further, the guidance provided by the assembly system also lower the requirements on training and education for the persons performing the assembling.

By means of the present invention, technical assistance and guidance is provided to the operator, thereby in an automated or semi-automated fashion helping the operator to identify a new item, and thereby greatly assisting in the assembling procedure. This helps the operator to identify the different tools, and eases the sorting and assembling process.

The arrangement of the picked items in the temporary storage area also assists in assembling the sets in the right order, and in a convenient and reliable way. The temporary sorting provides an overview for the operator, and makes the process faster and more controllable. It also makes every step in the procedure traceable and controllable, which increases the overall quality.

In practical experiments, it has been found that the new system significantly lowers the lead time, and also significantly decreases the need for prior training and supervision to perform the work, and still obtaining the same or even higher output quality.

The system of the present invention is also compact and very cost-efficient in that it requires low investments, and may easily be implemented in existing facilities, such as in presently available clean rooms arranged between cleaning areas and sterilization areas.

The new system is also compliant with all demands regarding clinical environment, and provides ergonomic advantages, since it provides improved work space, minimizes the required movements, and provides easily accessible input, output and storage areas.

The new system also minimizes the risk of errors during assembling, and is capable of handling a very large number and variety of medical instruments and/or pharmaceutical products.

The new system also enables the use of a standardized work process and the opportunity to trace the assembled sets over the entire procedure.

The identification unit preferably comprises an optical identification unit, such as a camera. The optical identification may be based on recognition of a machine readable optical identification, such as a bar code or a QR code, or based on other optically determinable features of the object, such as size, geometrical shape, certain dimensions, etc. Additionally, or alternatively, the optical identification unit may comprise a radio frequency identification reader, for reading of an RFID code. Additionally, or alternatively, the identification unit may comprise a weighing unit, such as a scale or weight sensor. Thus, the identification of the medical instrument and/or pharmaceutical product is preferably based on recognition of at least one, and preferably several, of: a machine readable optical identification, such as a bar code or a QR code, a radio frequency identification (RFID), physical dimensions, physical shape, and weight.

The input and output areas may be different areas, allowing simultaneous sorting and packing. However, preferably sorting and packing are performed sequentially, and for such use the same area may advantageously be used both as input area and as output area. Thus, a first tray or container may be arranged at the input area with a new batch of items, and when sorting has been completed, a second tray or container may be arranged at the same location for packing.

The temporary sorting area may be realized in various ways, and may comprise a single part or multiple parts. In one preferred embodiment, the temporary sorting area comprises a table surface comprising a plurality of visual indications. The visual indications may be realized in various ways, such as providing light sources in or beneath the table surface. In particular, the table surface with said visual indications may comprise a transparent or semi-transparent top cover, and a LED plate formed by a plurality of LED circuit boards beneath said top cover. It has been found to be of particular advantage to use LED circuit boards having a quadratic or rectangular form, and a break line extending along at least one of the two diagonals. However, alternatively other types of visual indications may be used, such as a remote light source, such as a laser, which is moveable to illuminate desired points or areas on the table surface. Further, the visual indications may be realized in the form of a display, such as a touch screen, being arranged in or beneath the table surface or entirely forming the table surface. Temporary storage positions arranged on a table surface are very versatile, and can be used for essentially any type of item.

Additionally, or alternatively, the temporary sorting area may comprise at least one of shelves and hooks, arranged on a supporting structure, such as a vertical wall. In particular, it has been found that hooks or hangers are very efficient for certain objects enabling hanging, such as scissors, and provide a very compact storage. Shelves, preferably with clearly separated compartments serving as temporary storage positions, are more versatile, and also provides relatively compact storage.

The system also preferably comprises a display arranged to display information to the user about at least medical instrument and/or pharmaceutical products to be picked in accordance with a set order. The display is preferably a touch screen, also allowing input from the operator.

The system may comprise a confirmation button, preferably arranged on said temporary sorting area or on the identification area, and communicably coupled to said controller. The confirmation button allows the operator to confirm some or all of the steps in the procedure in a swift way, such as confirming identification and placement at a temporary storage position during sorting and picking and packing of objects during packing. Such confirmations enhance the traceability and quality of the operation and of the system.

The system may also comprise a label writer being communicably coupled to said controller. Hereby, a label may be printed and attached to packed sets after completion of the packing, so that the packed set is subsequently identifiable and labeled as complete or incomplete.

The system may also be referred to as a workstation. The workstations are preferably adapted to be arranged together, to form a workstation assembly or a workplace arrangement. In such a workplace arrangement, the systems or workstations are preferably arranged back-to-back, in a triangular or quadratic configuration. This is a very space efficient and compact way of arranging the workstations, and also enables at least one shared resource arranged between the systems. For example, resources such as cleaning equipment, drying equipment, compressed air equipment, sealing equipment and/or the like may be arranged between the workstations at the corners, allowing these resources to be shared between two or more workstations.

A workstation assembly also enables efficient staffing, since competence and experience may easily be shared. For example, a group of four workstations may be staffed by one highly competent and experienced chief operator and three less trained and experienced assisting operators. Since the operation of the workstations are highly automated, the particular need for high competence is not very frequent, and a single chief operator may deal with all such situations for all the workstations.

According to another aspect of the invention, there is provided a method for assembling sets of medical instruments and/or pharmaceutical products, the method comprising:

receiving a batch of unsorted medical instruments or pharmaceutical product containers;

automatically identifying with a controller one medical instrument or pharmaceutical product container at time using an identification unit;

assigning with the controller an empty storage position in a temporary sorting area to the identified medical instrument or pharmaceutical product container;

visually indicating the assigned storage position with the controller;

acquiring a set order in said controller; and visually indicating, with said controller, occupied storage positions in said temporary sorting area one at a time in accordance with the set order.

With this aspect of the invention, similar advantages and preferred features are present as in the previously discussed first aspect of the invention.

These and other features and advantages of the present invention will in the following be further clarified with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 5 is a schematic illustration of an exemplary visual indication of a temporary storage position on a table surface;

FIG. 6 is a schematic illustration of LED circuit boards for use in the LED plate of FIG. 4;

DETAILED DESCRIPTION OF PREFERRED EMBODIMENTS

In the following detailed description, preferred embodiments of the present invention will be described. However, it is to be understood that features of the different embodiments are exchangeable between the embodiments and may be combined in different ways, unless anything else is specifically indicated. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

A method and system for assembling medical instruments will first be discussed, for use e.g. when assembling cleaned medical instruments prior to sterilization.

Figure 1:
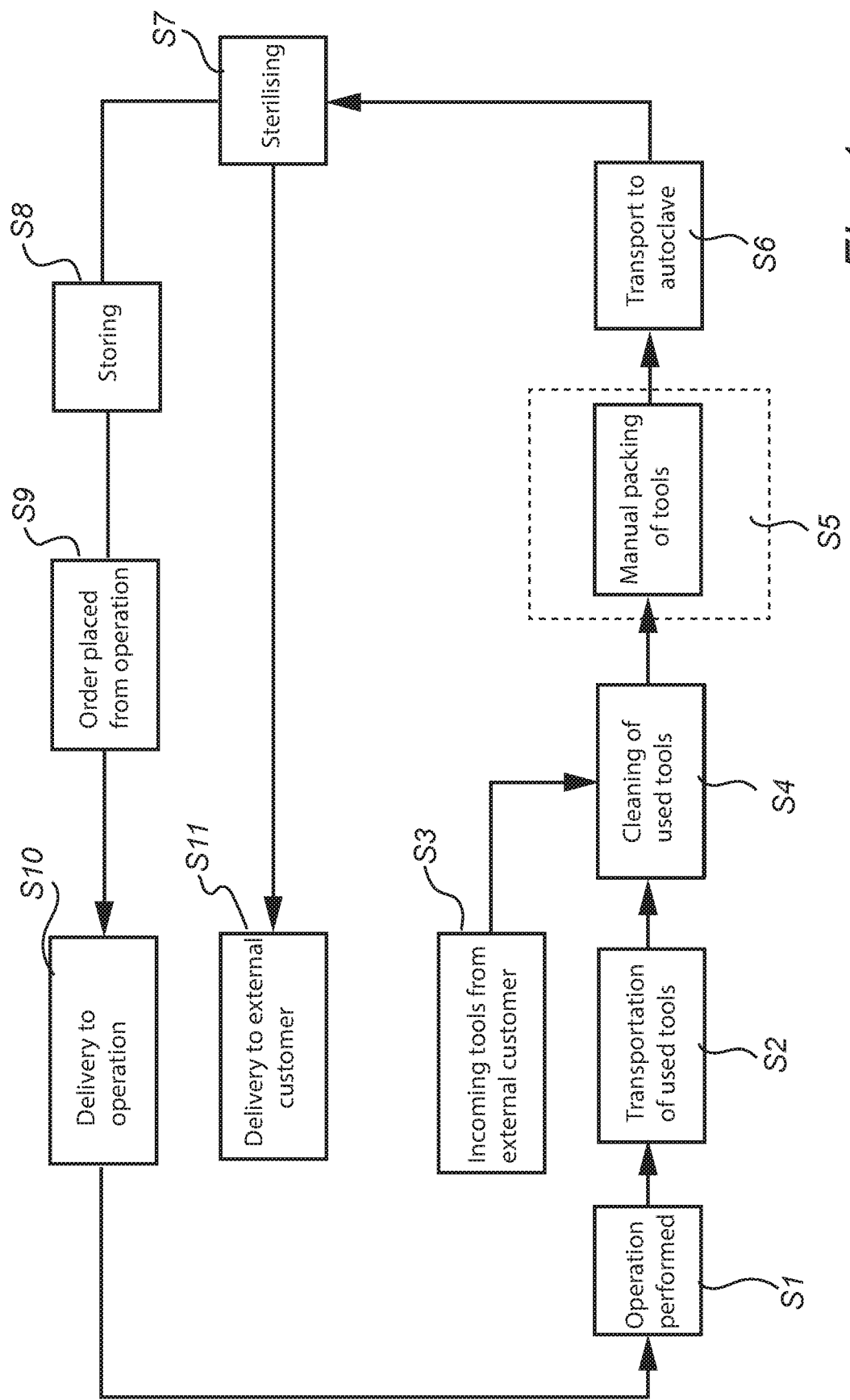
FIG. 1 is a flow chart generally illustrating a cleaning and sterilization process.

A general cleaning/sterilization process in a cleaning facility is illustrated in FIG. 1. Instruments are used in a surgical procedure, step S1, and are thereafter transported to the cleaning facility, step S2. Medical instruments may also be received from external customers, step S3, or purely from external customers, in case the cleaning facility is an independent operation. The used tools are then cleaned in a dishwasher or the like, step S4. Thereafter, the now cleaned medical instruments are inspected and sorted into appropriate sets in an assembling step S5. The method and system to be disclosed in the following are particularly concerned with this step of the overall procedure. The sets are then forwarded to a sterilization equipment, such as an autoclave, step S6, and sterilized, step S7. The now sterilized sets may then be stored, step S8, and upon request, step S9, the requested set(s) is delivered to the surgery site, step S10. Alternatively, the sterilized sets may immediately be delivered to external customers, step S11.

It has been found that the assembling step, i.e. the sorting and packing part, is often the bottleneck of the overall process, and is also very sensitive to quality problems. It is therefore very advantageous to reduce the lead time, improve quality and increase cost-efficiency in this step.

Figure 2A:
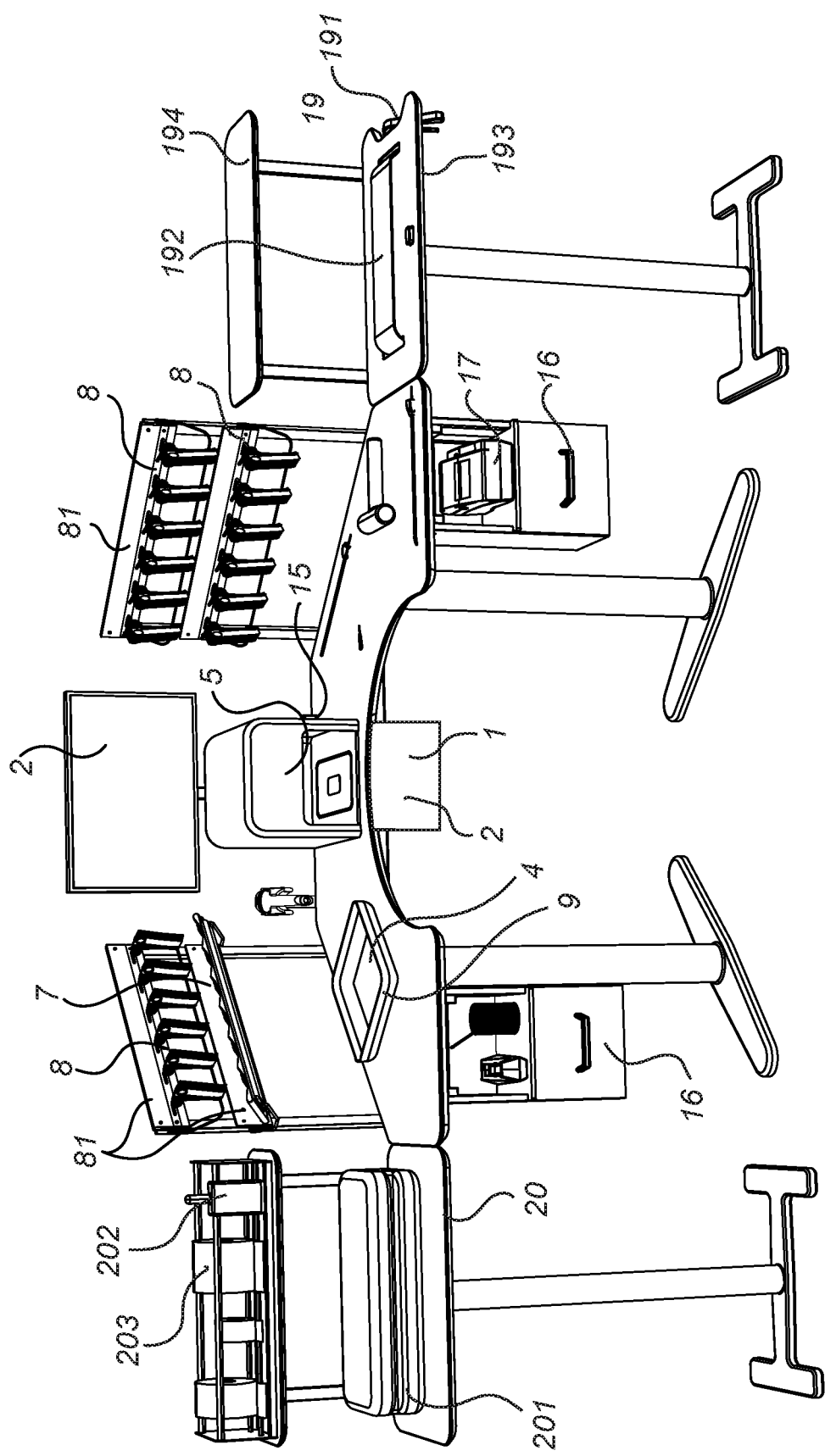
FIG. 2a is a front view of a workstation in accordance with an embodiment of the invention.
Figure 2B:
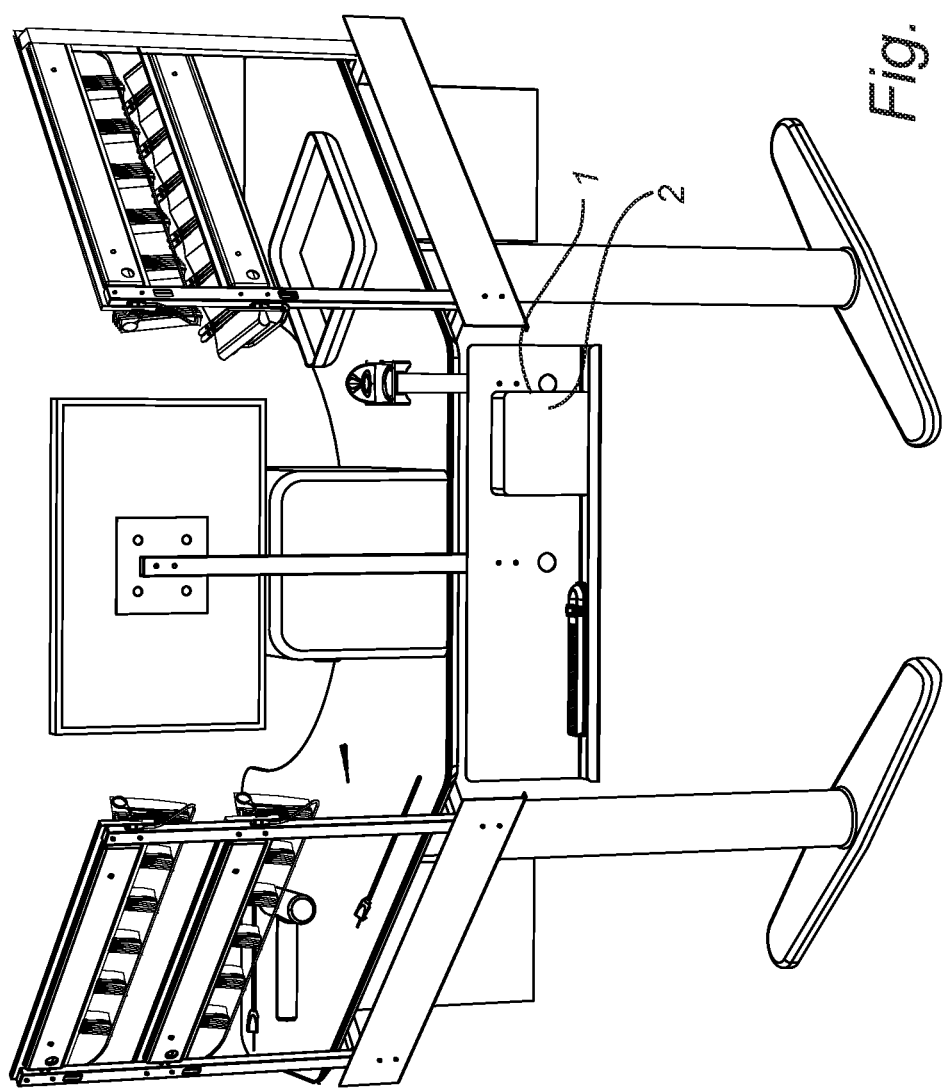
FIG. 2b is a backview of the same workstation.

An assembling system, in the form of a workstation, will now be discussed in further detail with reference to FIGS. 2a and 2b. The system comprises a controller 1, which may be arranged as a processor or computer at the workstation, or be a remote controller, connected to the workstation by wired or wireless communication. In the illustrative example, the controller is arranged as an integrated unit together with a display 2.

The controller is further connected to a database, arranged in a data storage 3, comprising data objects corresponding to available medical instruments or the like. The data objects may comprise identification data related to the objects, such as identification codes, sizes, dimensions, shapes, etc. The data objects may also comprise images of the objects, names, quality check parameters, etc The database may be arranged integral with the controller, or be arranged as a separate unit connected to the controller by a wired or wireless connection.

The workstation further comprises an input area 4, in which batches of items to be sorted is received. The batches may be received in the form of trays, boxes or the like. In particular, when the items are cleaned medical instruments, the item batches may be received from a dishwasher or the like.

The workstation is further provided with an identification area, comprising one or more identification unit(s) 5. The identification unit(s) preferably comprises an optical identification unit, such as a camera. The camera may be arranged above the identification area. The optical identification may be based on recognition of a machine readable optical identification, such as a string of characters or numbers, a bar code or a QR code, or based on other optically determinable features of the object, such as size, geometrical shape, certain dimensions, etc.

The identification unit(s) may additionally, or alternatively, comprise a radio frequency identification reader, for reading of an RFID code.

The identification unit(s) may also, additionally, or alternatively, comprise a weighing unit, such as a scale or weight sensor. The weighing unit may preferably be arranged below the identification area.

The identification unit is preferably adapted for machine vision, and comprises one or more cameras. The information received may then be processed by the controller to identify the object.

Since the identification unit will during use be used very frequently it is located right in front of the operator to ensure an ergonomic work position. This means that the operator can place the items in the identification unit, and at the same time look at the display where necessary information can be displayed.

The machine vision can be used to identify the object by reading a printed text, numbers, bar codes, and the like, indicating e.g. a model number. Additionally, or alternatively, the machine vision may be used to determine the shape, size or the like of the object, and thereby identifying the object.

Moreover, by including a scale in the identification unit, the identification process can be further improved. The weight of the tools can help the system to narrow down the possible alternatives to a minimum and thereby the identification can become even more accurate.

The identification unit may also be used as an electronic magnifying glass during the quality check. When the operator needs to examine a tool closely the identification unit can be used to present a zoomed in picture of the tool on the display together, and information about common problem areas for this type of product may also be displayed together with the image.

Thus, the identification of the medical instrument and/or pharmaceutical product is preferably based on recognition of at least one, and preferably several, of: a machine readable optical identification, such as a text or numbers, a bar code or a QR code, a radio frequency identification (RFID), physical dimensions, physical shape, and weight.

In use, the operator picks a random item from the input area and places it on the identification area. The identification unit(s) then acquires information about the item, and the data is forwarded to the controller. The controller then compares the acquired data with the data in the database, and in case of a match, identifies the item as a specific data object stored in the database. Hereby, the item may be identified as a specific medical instrument or pharmaceutical product container automatically. In case no match is obtained, the controller may issue an alarm, request manual input or the like. However, if the database is complete, covering all available medical instruments and/or pharmaceutical product containers, a no-match would seldom occur, and only be due to damaged items and the like. Thus, a no-match may also be an indication of a quality problem, and the no-match item may need to be replaced. However, if a manual input is requested, the system may automatically identify and display a selection of the most probable candidates to the user, thereby facilitating the manual input. Further, the system may be a learning system, whereby the manual input, whenever received, is used to improve the identification process over time.

The workstation further comprises a temporary sorting area comprising a plurality of storage positions for medical instruments and/or pharmaceutical product containers.

In the illustrated embodiment, the temporary sorting area comprises a table surface 6, a shelf 7 and several sets of hooks or hangers 8, e.g. arranged on a supporting structure, such as a wall. However, the temporary sorting area may comprise only one or two of table surface, shelf and hangers, and other forms of temporary sorting areas are also feasible, such as trays, bins etc.

The temporary sorting area provides a plurality of storage positions. Each storage position is provided with a visual indication, so that a visual indication of one any of the storage positions can be made at any time, and so that the storage positions can be visually indicated in any determined sequence. The visual indication may comprise a lamp, a light bulb, an LED or the like, providing a light of a determined color, which may be activated to indicate the position. However, the visual indication may also be provided by a small display, by mechanically moveable indicators or the like.

Thus, when an item has been identified at the identification area, the controller decides a suitable temporary storage position for the item, selected from the temporary storage positions which are still not occupied, and stores the selected temporary position in association with the item identification.

In case one or several lights are used for indication, the light may be a steady, continuous light, or a flashing light, varying in intensity over time. The lights may also be of the same color, or may have different colors. For example, different colors may be used in the first phase of the procedure, when items are placed out in the temporary sorting area, and in the second phase, when items are picked from the temporary sorting area to be assembled to a specific set.

The system further comprises an output area 9, arranged to receive medical instruments and/or pharmaceutical products as assembled sets. The output area may e.g. comprise a suitable tray, container or the like, arranged to house an assembled set of medical instruments or pharmaceutical products. Since the first phase of the assembling procedure, i.e. the placement of items in the temporary sorting are, and the second phase of the assembling procedure, i.e. the picking of items from the temporary sorting area into assembled sets, generally occurs sequentially after each other, the input area and the output area may be one and the same area, as in the illustrated example. However, alternatively, different areas may be assigned for the input area and the output area.

The workstation is preferably provided with a curved shape, when seen from above, thereby partly encircling or embracing an operator standing centrally in front of the workstation. This enables the operator to reach all parts of the workstation with a minimum of movement and effort.

Thus, when the incoming instruments or pharmaceutical products have been temporarily stored in the temporary storage area, a suitable set order is selected in the controller.

The controller thereafter selects an item at a time from said set order list, and visually indicates the storage position in the temporary storage area where the selected item is stored, thereby guiding the operator to pick the selected order.

The display 2 may be used to show details about identified items, during the identification phase, to aid in assigning and showing the temporary storage position selected for the identified item, to enable selection of a suitable order list, to aid in picking the correct item for a selected order list, etc. For example, the display may be used to show a picture or image of an item to be picked, to show progress of the picking on a list, etc.

The system may also comprise an input device, such as a keyboard, buttons, switches or the like, communicably coupled to the controller. Preferably, at least a confirmation button is provided, and e.g. arranged centrally in the work station, and in front of the display. In the illustrated exemplary embodiment, a confirmation button 15 is placed on the side of the identification unit. The confirmation button may be used to confirm completion of steps, such as temporary storing at a selected position, completed picking to the output area, and the like. It may also be used to select among various alternatives, such as for selecting a particular order list, etc.

Additionally, or alternatively, the display may also be a touch screen, allowing user input by touching particular areas on the screen.

The workstation preferably comprises or forms a table, with a table surface 6 and a frame 10. The frame preferably comprises a height adjustment mechanism, allowing the height of the table surface to be changed.

The temporary storage area will now be discussed in further detail. The temporary storage area comprises one or several of a table surface, hangers and shelves. All parts of the temporary sorting area are provided with visual indications, such as LEDs, making it possible for the controller to visually indicate temporary storage positions in the temporary sorting area, for indication of where an item should be placed during sorting, or from where an item should be picked during assembling.

The table surface, also referable to as the main surface, preferably comprises a plane surface, and a plurality of light points, light areas or light lines arranged in or beneath the surface, on parts of the table surface forming a temporary storage area. Hereby, one or several areas/lines/points may be activated to determine a particular spot on the tables surface, or to visually indicate an area. In case an area is indicated, this area is preferably dimensioned and shaped to resemble the item to be placed on the temporary storage position.

Figure 3:
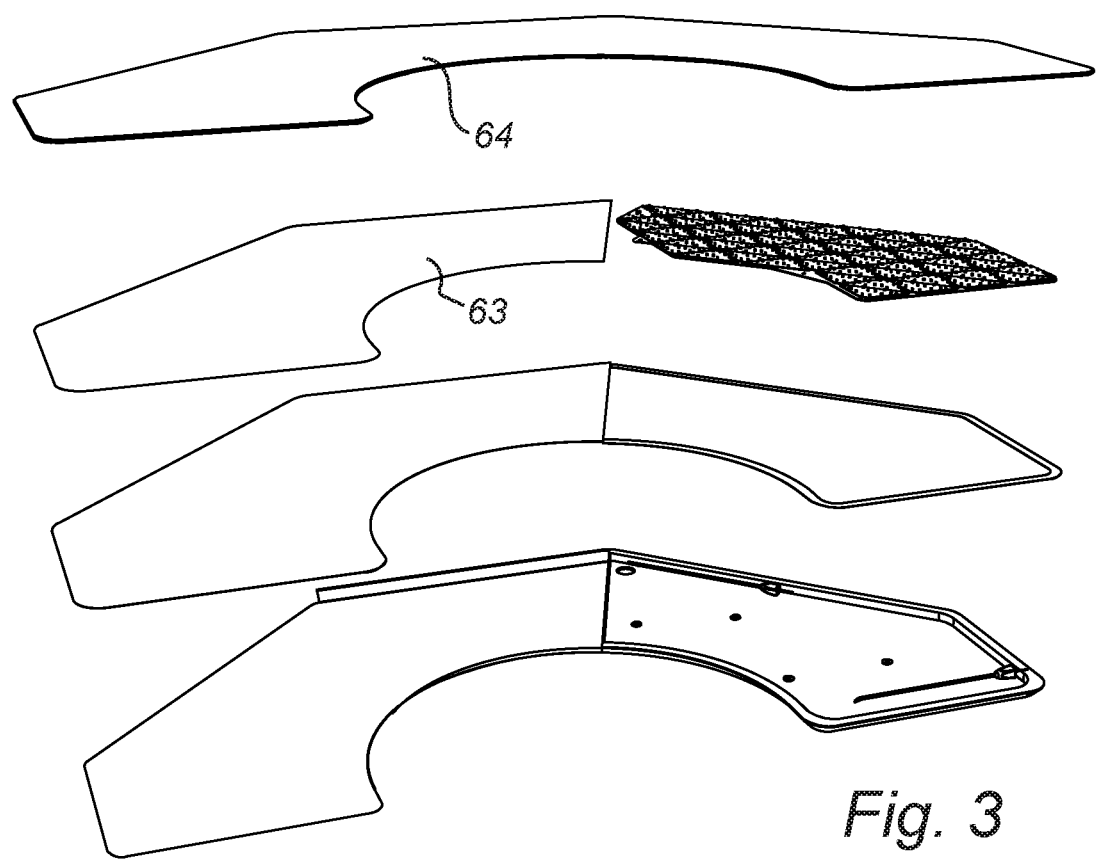
FIG. 3 is a schematic exploded view of a table surface in accordance with an embodiment of the present invention.

In one embodiment, the table surface comprises several parts, as illustrated in FIG. 3. The table surface may comprise a top cover 61, a LED plate 62, a base plate 63, and an optional friction sheet 64 arranged between the top cover and the LED plate and/or the base plate. The base plate is preferably provided to cover the areas not covered by the LED plate. However, the LED plate may alternatively extend over the entire temporary storage area, whereby no base plate is needed.

The top cover is preferably transparent or semi-transparent, i.e. at least to some extent transparent. Since the top cover is placed on both the base plate and the LED plate, this is the surface onto which the items are placed. The top cover need to be transparent enough to enable light to penetrate through the material. At the same time, it is preferred that the material is not entirely transparent, so that the top cover make the underlying circuits etc invisible. Thus, a semi-transparent material is preferred, such as a transparent material having a frosted finish. This can either be achieved by frosting the actual top cover or by attaching a thin frosted sheet on the bottom or top side of the top cover.

The optional friction sheet increases the friction so that the top cover stays in place without the need of any fasteners which contributes to an easier cleaning process. Moreover, the friction sheet preferably has a dampening effect, so that the noise from items touching the top cover is also minimized. Since the top cover covers both the base plate and the LED plate there is no visible gap between the two parts which contributes to an easy cleaning process.

Figure 4:
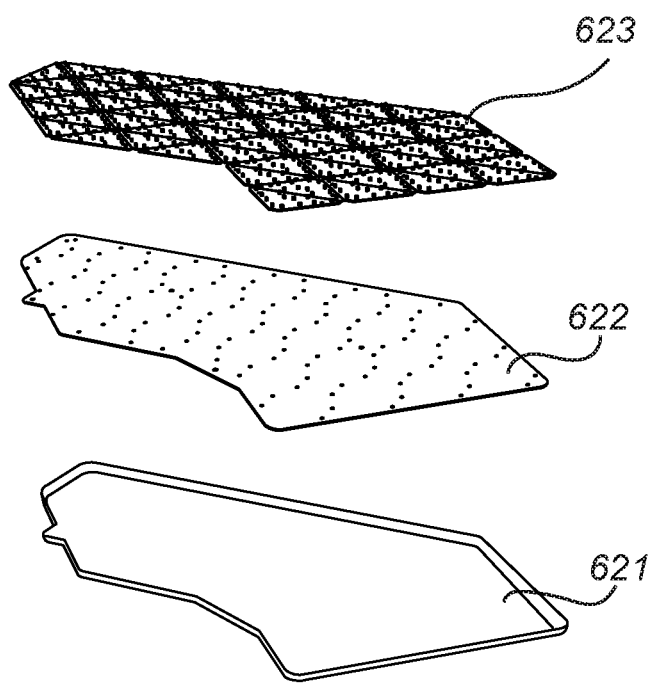
FIG. 4 is a schematic exploded view of a LED plate of a table surface in accordance with an embodiment of the present invention.
Figure 7A:
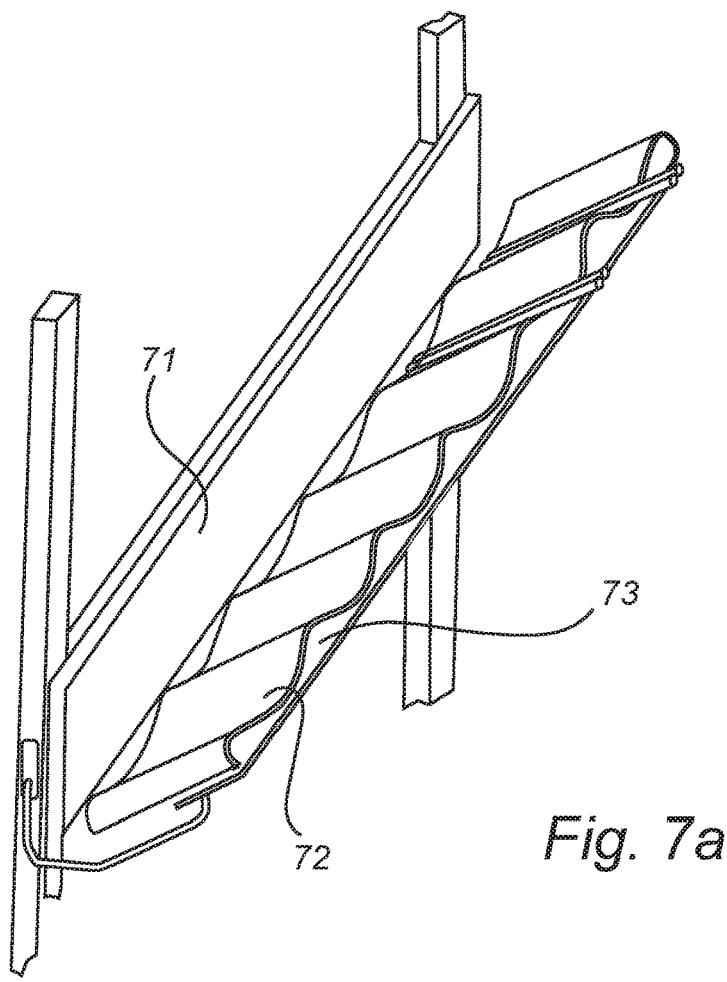
FIGS. 7a and 7b are a detailed view of a shelf of the workstation of FIG. 2.
Figure 7B:
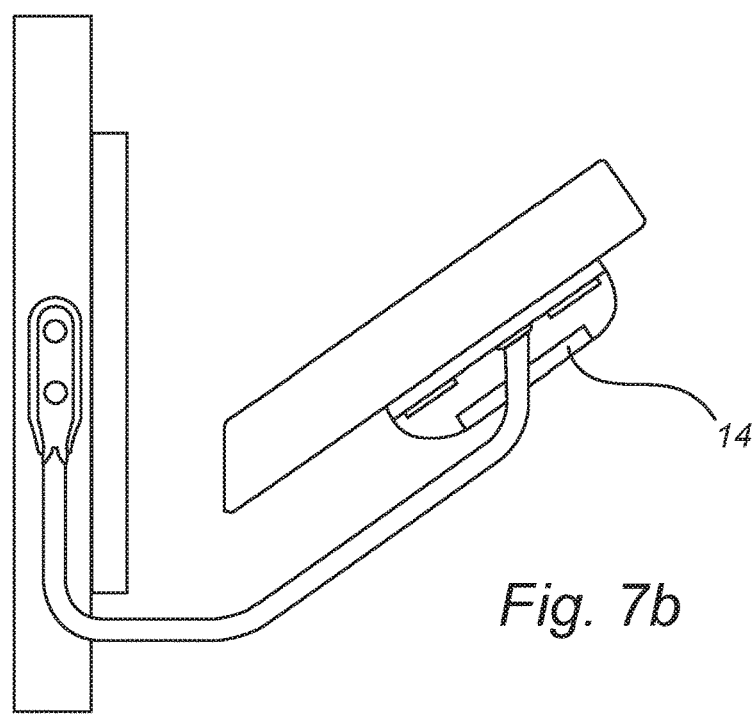

The LED plate is illustrated in further detail in FIG. 4. The LED plate preferably comprises a back cover 621, which may be fixed in the frame 10 of the workstation. Inside the cover there are circuit boards 623, e.g. mounted on an optional attachment plate 622. The circuit boards 623 comprises a plurality of LEDs.

The purpose of the LED plate is to create a temporary storing position for the tools. For example, the LEDs may be used to illuminate rectangles corresponding to a dedicated storage position. An example of this is illustrated in FIG. 5. Here, a hammer 11 has been identified, and is assigned a dedicated temporary storage position 12. A rectangle is then illuminated by activating an appropriate set of LEDs, illuminated either with steady light or with flashing light, thereby making the assigned temporary storing position 12 visible. The dimensions of the rectangle preferably correspond to the dimensions of the item, i.e. the hammer in this example. The dimensions of the items are known by the system, and available to the controller once an item has been identified. Hereby, a very exact positioning of the item at the temporary sorting area is provided. Instead of rectangles, the LEDs may be controlled to illuminate an area which also is shaped in accordance with the item to be placed, such as in the form of a larger rectangle at one end and an elongate narrow rectangle at the other end when a hammer is to be placed. Hereby, even more precise control of the temporary sorting area is provided. The fine control of the placement on the temporary sorting area allows the temporary sorting area to be used more efficiently, allowing a denser arrangement of the items. However, alternatively, a storage area may be visualized by means of a single LED, LEDs arranged along a single line, or the like.

To enable an efficient use of the table surface available to be used as a temporary sorting area, the LED circuit board(s) is/are preferably shaped to fill the available area as far as possible. In a preferred embodiment, the LED circuit boards are relatively small and with an essentially triangular shape. Alternatively, the LED circuit boards 623' may be formed as rectangles, and preferably with a quadratic shape, and with a weakening forming a break line 6231 along one or both diagonals. Hereby, the quadratic LED circuit board can be broken into two triangular boards, or into four triangular boards, if two break lines are provided. Such an embodiment, with one breaking line 6231, is shown in FIG. 6. It has been found that this shape is easy and cost-efficient to manufacture, and allows a good filling of most areas, regardless of shapes and dimensions. Thus, it is possible to obtain a good filling of randomly sized and shaped areas by means of a cost-efficient, using standardized LED circuit boards. The quadratic boards may e.g. have a 100×100 mm size. This configuration means that only one standardized size has to be produced but two sizes are available when fitting them on the plate. This is illustrated in FIGS. 4 and 6. On each of the circuit boards there are a plurality of LEDs 6232, such as 12 or 24 LEDs on each, depending on size.

FIG. 6a shows a LED board in the original, quadratic shape, FIG. 6b shows a LED board of a triangular shape, obtained by breaking the LED board of FIG. 6a into two, and FIG. 6c shows an example of how a surface may be filled with such quadratic and triangular boards.

Additionally, or alternatively, the temporary sorting area may comprise wall sections 13 arranged at the outer periphery of the workstation. In the illustrative example of FIG. 2, two such wall sections 13 are provided, one to the left of the centrally located display 2, and one to the right of the display. The wall sections may be formed by plates, forming solid walls, or by bars or the like, forming a non-solid wall. In the illustrative example of FIG. 2, the wall sections are formed of bars, whereby the wall sections comprise a plurality of wide openings. The wall sections may be provided with shelves 7 and/or hangers 8, forming temporary storing positions, and each storage position being visually indicatable, e.g. by means of LEDs or the like.

In the exemplary embodiment, the wall section 13 to the right comprises two rows of hangers 8, and the wall section to the left comprises one row of hangers 8, and one shelf 7. LEDs or other form of lighting may be provided in plates 71, 81 arranged behind the shelf 7 and the hangers 8, respectively. In a preferred embodiment, the LEDs are arranged on one or several circuit board(s), and arranged behind a cover of transparent or semi-transparent material, similar to the LED area in the table surface, as discussed in the foregoing. Further, a backside cover may be provided behind the LED circuit board(s). Preferably, at least one LED is designated for each hanger 8 and for each storage position formed on the shelves 7.

Since a large amount of the medical instruments are suitable for hanging, hangers 8 offer a very space efficient way of temporarily storing such items.

The distance between the rows of hangers may be chosen so that some hangers are suitable for relatively long items, whereas other hangers are suitable for relatively shorter items. Further, the hangers may be adapted for carrying a single item, or be adapted for carrying a plurality of items, such as a plurality of scissors of the same type.

The shelf 7 may be a conventional shelf, with a shelf surface extending in a horizontal plane. However, in a preferred embodiment, the shelf is arranged in an inclined, tilted disposition, so that the shelf surface is angled slightly upwards in a direction away from the wall section. Additionally, or alternatively, it is also preferred that the shelf surface is non-planar, and forms lowered portions 72, forming the temporary storage positions, and raised portions 73, forming partitions between the temporary storage positions. Additionally, or alternatively, it is also preferred that the shelf is not in direct contact with the wall section, so that there is a gap formed between the backend of the shelf surface and wall section, and in particular the plate 71. The gap may a few centimeters wide. This gap facilitates cleaning of the shelf and prevent dirt from accumulating.

The workstation may also comprise integrated lighting, and in particular for illuminating critical areas where light is most essential, such as over the input and/or output area. Thus, lights may be provided at one or several suitable locations on the workstation. For example, a light 14 may be arranged beneath the shelf 7, to illuminate the input and/or output area. Lights may also be arranged underneath the table surface, e.g. in the vicinity of drawers to be discussed in the following, or over additional table surfaces, also to be discussed in more detail in the following.

The workstation may also be provided with one or more drawer 16 underneath the table surface. Preferably, two drawers are provided. The drawers may be arranged on each side of the main surface. The drawers can be used to store additional equipment and material needed for the sorting, assembling and packing. For example, a drawer could contain tape, pens, straps and the like.

The workstation also preferably comprises a label printer 17. The label printer may be arranged in one of the drawers, as in the exemplary embodiment shown in FIG. 2, but may also be arranged at other locations in the workstation. The label printer may e.g. be used to print labels to be attached to assembled sets, thereby enabling identification of the assembled sets at later stages. The labels may also be used to provide easily accessible information about whether the set is complete or not.

The workstation may also comprise a barcode scanner 18, or reading barcodes. The barcode scanner may be used as a complement to the identification unit. However, primarily, the barcode reader is intended to read barcodes on incoming or outgoing trays or containers. The barcode scanner may e.g. be arranged on the left side of the display, as in the illustrative example, where it can easily be accessed.

At one or both sides of the main surface, additional table(s) may be provided, either as additional, extra tables, or as additional table surfaces connected to the main surface and/or the frame. In a preferred embodiment, the additional table(s) are provided on additional, extra table(s), and preferably one additional table is arranged on each side of the main surface.

On one side of the main surface, in the illustrative example illustrated in FIG. 2 on the right side, the additional table 19 comprises an additional drying/checking station. The drying/checking station comprises a compressed air nozzle 191. The compressed air may be used to dry items, or to perform a function check of certain items. The compressed air nozzle, or compressed air gun, may be located on the right side of the table and be attached to the table using a magnet which keeps it in place when it is not used.

The drying/checking station may further comprise a rotating towel sheet 192. The rotating towel sheet is preferably arranged centrally on the table surface. The rotating towel sheet may be activated by a separate button 193. The rotating towel sheet is primarily used to see if the items contain any liquids or dirt. For example, the operator may blow air through tubes and the likes towards the towel, thereby verifying whether there is dirt left after cleaning. It is basically a towel that is placed on the table and when it is wet the operator presses the button to make it rotate, or rotate it manually, so that a dry area is shown. When necessary, it is possible to replace the towel. Above the rotating towel sheet there a shelf 194 may be provided for storing necessary products.

On the other side of the main surface, in the illustrative example illustrated in FIG. 2 on the left side, the additional table surface 20 comprises a device for packaging the assembled set in a sterilization bag or the like. The device may comprise a sealing equipment 201 for sealing bags, and a cutting device 202 and a plastic bag dispenser 203 arranged on a shelf above the sealing equipment.

There is often a need for several workstations in an assembling facility. The workstations as discussed in the foregoing are very well suited to be arranged close together in a very space-efficient way. Thus, the workstation is preferably adapted to be arranged with one, two or more additional workstations, to form a workstation assembly. The work stations are preferably arranged back-to-back, so that the operators in the default working position are facing the center between the workstations. In case four workstations are used, the workstation assembly will preferably assume a quadratic formation, whereas a workstation assembly of three workstations will preferably assume a triangular formation.

Figure 8:
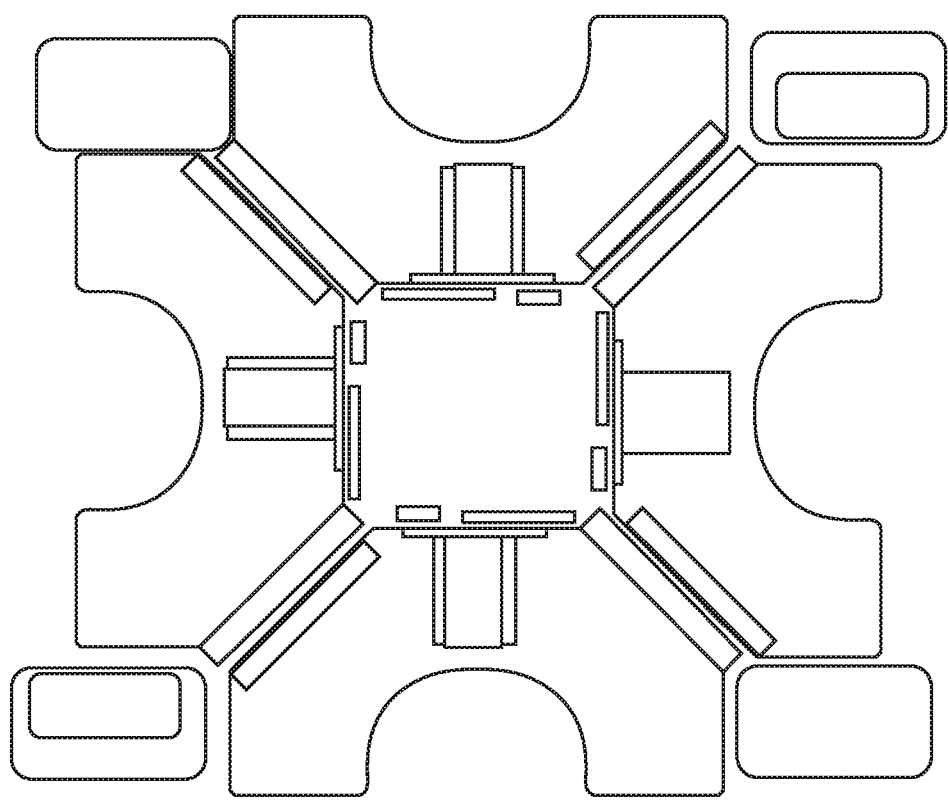
FIG. 8 is a top view of a workstation assembly comprising four workstations in accordance with FIG. 2 assembled together.

In one embodiment, as illustrated in FIG. 8, the workstation assembly comprises four workstations of the previously discussed type assembled together. The workstations preferably have slanted sides at the sides farthest from the operator, and preferably being arranged in essentially 45 degrees inclination compared to the width direction, i.e. the direction extending from one additional table to the other additional table. Hereby, the workstations can be arranged relatively close together, forming only a small central opening between the workstations.

However, other inclination angles may be used in case the workstation assembly should comprise e.g. 3, 5 or 6 workstations instead. In case only two workstations should be provided, the backside of the main surface may be straight, without any slanted sides.

The provision of a central opening between the workstations is not mandatory, but may often be preferred. This central space may e.g. be used to accommodate electronics, pneumatics, and other shared resources. It may also accommodate a central electric central, or electric contacts, and the like. If the room has poles or similar structures the workstation assembly can also advantageously be arranged around this structure, thereby making efficient use of the available space.

In this way, several workstations can be provided in a limited area. Further, by working so close together, it also becomes possible to seek assistance from any of the other operators when needed. The workstation assembly of this type can be operated by four operators of which only one need to be highly experienced, whereas the other operators may have less education and experience. The semi-automated system as discussed above makes situations where manual identification of items and the like rare, and this capacity can then be shared between the workstations in a very efficient manner.

Further, parts of the workstations that are less frequently used during operation may also be shared between the workstations. In particular, the additional tables 19 and 20 may be shared, so that only four additional tables 19, 20 are used, and arranged in the corners between the workstations, thereby becoming easily accessible for each operator.

A possible work process at the workstations will now be discussed in more detail. The workstations as discussed in the foregoing ensure that the assembling process, involving sorting and packing, is carried out in the same way by all operators.

Figure 9:
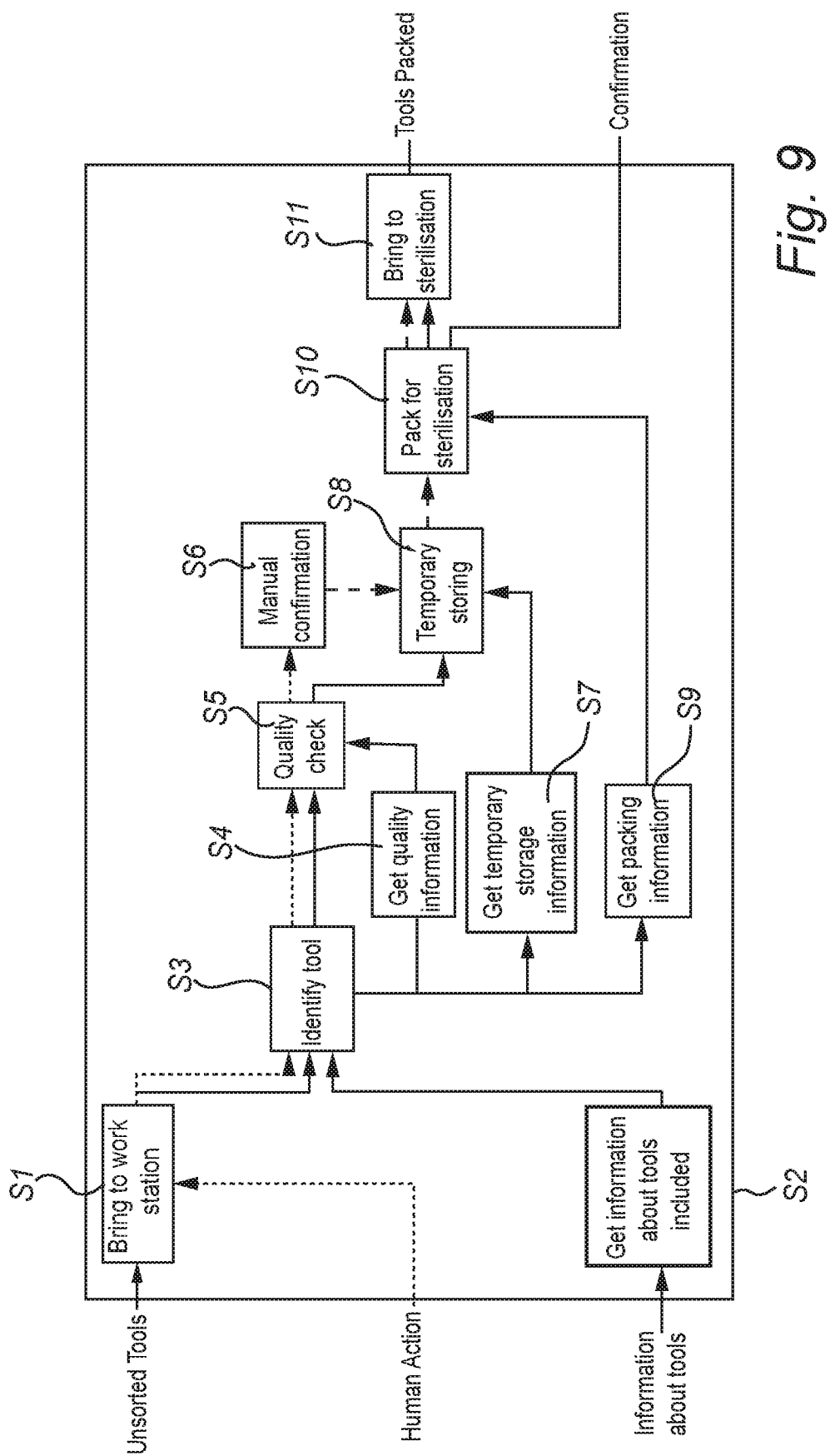
FIG. 9 is a flow chart generally illustrating an assembling process in accordance with the present invention.

As a first step S1 in the process, illustrated schematically in FIG. 9, new items, such as medical tools, are brought to the workstation. In many cases, information is accessible regarding which types of items the tray/container contains. For example, such general information may be stored in the database, and may be accessible by entry of an identity of the tray/container or the like. For example, the tray/container may be provided with a barcode, and by scanning the barcode, the controller may automatically retrieve the relevant data from the database. Thus, as an optional second step, S2, general information, whenever present, is retrieved. This general information may e.g. relate to what type of set that it is related to, which items that are expected to be there, and other useful information.

Then, in a subsequent step S3, an item is brought from the input area and is identified. Identification is preferably made automatically, by placing the item in the identification area, whereby the controller will automatically identify the item in the way discussed in the foregoing. In case automatic identification is not possible, the controller may display various possible alternative identifications on the display and request that the operator selects the correct one. A similar identification routine may also be used for items which for some reasons, e.g. due to size, cannot be placed in the identification unit, or when the set comprises only a limited number of relatively easily identified items. Thus, alternatively, the controller may display the possible alternatives on the display, so that the operator may select the appropriate choice. The possible alternatives are preferably presented as images, and possibly with additional text in relation thereto. Selection can be made in various ways, and e.g. by touching the appropriate area on the touch screen. It is also possible for the operator to input an identity, a model number or the like directly into the system, e.g. by operation of the touch screen. Whenever an identity has been selected, regardless of whether identification has been obtained automatically or manually, the operator is preferably requested to confirm the identification, e.g. by pressing a confirmation button. Hereby, it is ensured that confirmation of the identity also by human action is obtained.

Once the identity has been obtained, the controller preferably retrieves quality information from the database, step S4, and displays it to the operator. This information preferably comprises information about how the quality check should be performed, etc. However, if quality check is not needed, or if quality check can be performed without any assistance, this step may be omitted.

If required, the item is then checked for quality, step S5, and the operator is preferably requested to confirm that the quality is adequate, e.g. by again pressing the confirmation button, step S6.

The quality check may also require additional cleaning or drying of the item, and may e.g. require use of compressed air.

During the quality check, the operator may again use the identification unit, to magnify certain parts of the item, etc. By use of the identification unit, quality check may also, at least to some extent, be made automatically. If a quality problem is determined, the operator, or the controller in case of an automatic quality check, may make a note about this in the system, and the operator may also be requested to replace the item.

The controller also determines a suitable temporary storage position in the temporary sorting area, step S7, and indicates this to the operator by the visual indication as discussed above, such as by continuously or intermittently activating a light, such as a LED, at the selected storage position. A suitable temporary storage position may be determined based on the size of the item, properties of the item, the space available and/or the order in which the items are to be picked for packing. The operator then places the item at the dedicated temporary storage position, step S8, and may also confirm this by again pressing the confirmation button or the like.

Steps S3-S8 are then repeated until all items that have been received in step S1 have been identified and sorted out at dedicated storage positions on the temporary sorting area.

The controller also retrieves a set order for packaging, step S9. This order may be obtained automatically, and be based on the identification of the tray/container, or the identification of the items. However, it may also be retrieved based on user input, e.g. a user selection of a particular order list.

The items are then packed in accordance with the set order, and in an appropriate order determined by the controller, step S10. During packing, one item at a time is indicated to the operator by using the visual indication of the temporary storage position housing the particular item. The item to be packed may also be displayed on the screen. The controller may also present an image of the packed tray/container to be obtained.

The system may require the operator to confirm each item that has been packed, e.g. by again pressing the confirmation button.

When all tools are packed a label may be printed and attached to the tray/container. The tray/container may also be sealed in a plastic wrap or plastic container. The user may also be requested to confirm completion of the packing, again e.g. by use of the confirmation button.

As a last step, the packed tools are brought to sterilization, preferably together with a confirmation that the process was performed correctly, step S11.

The controller may also be able to handle credentials, and may e.g. request a personal log in and log out of the operator, thereby making the process traceable.

The repeated request to the operator to confirm any actions taken also makes the process traceable and controllable, and also ensures that the operator still has responsibility regarding the correctness of the performed work. The system may require a confirmation before allowing the process to continue. However, in case a more automated system is wanted, many of these confirmation steps may be omitted.

The selection of suitable temporary storage positions may be determined based on the size of the item, properties of the item, the space available and/or the order in which the items are to be picked for packing. In particular, it is preferred that the temporary storage positions are determined based on size, type of item and thereto related properties, and space available. The allocation algorithm ensures that all items are placed at their optimal position. For instance, is it preferable to use hooks for scissors since they are easy to hang and can easily be combined using a pin or the like during packing. The properties of the temporary storage positions are determined during installation and are stored in the system. For ergonomic reasons it is preferable to primarily use lower shelves and hangers, and primarily to use easily reached temporary storage positions on the table surface.

As an example, the controller may first determine if the item can be handed on a hanger. If so, it determines, based on size, whether it should be placed on a hanger for longer items or on a hanger for shorter items. The most easily accessible hanger of the hangers of this determined type being unoccupied is then selected to be the temporary storage position. If the item cannot be hanged, the controller may determine if it can be placed on a shelf, based on size etc. If so, the most easily accessible shelf storage positions of the shelf storage positions being unoccupied is selected to be the temporary storage position. If not, the most easily accessible and unoccupied temporary storage position on the table surface is selected. Unoccupied is in this context to be construed as not being full, since some temporary storage positions may accommodate more than one item of the same type. For example, a hanger may accommodate several scissors of a certain type.

If there is an item that cannot be placed on any of the temporary storage positions the software may tell the operator to place it at another area where it fits, called other area. This could also be the case if all possible temporary storing positions are full. This situation will however be very rare. Therefore, it need not be specified exactly where the operator should place the tool, only that it should be placed at an appropriate place.

A particular example of a workstation has now been discussed in detail. However, many alternative embodiments are possible. For example, other types of identification units are feasible, such as identification units using solely RFID recognition, using solely machine vision, and the like. Further, the temporary sorting area may be realized in various ways, such as having only hangers, only shelves, only a table surface, or any combinations of these. Other ways of providing temporary storage positions are also feasible, such as magnetic walls and the like.

Some such alternative embodiments will now be generally discussed.

Figure 10:
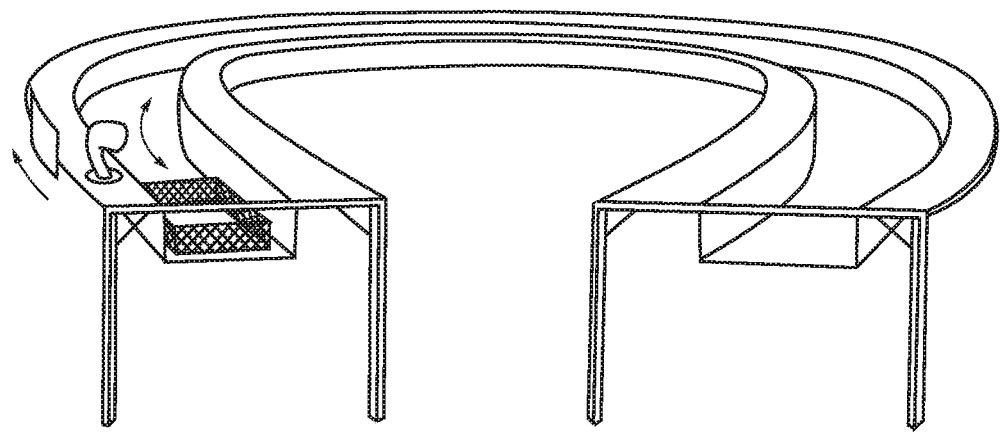
FIGS. 10-15 are schematic illustration of alternative embodiments of workstations in accordance with the present invention.

In FIG. 10, a workstation is illustrated comprising a table arranged in a curved shape, such as forming a semi-circle. The table has a guiding groove extending along the table, dimensioned to fit a tray/container. The table also has an identification unit, here in the form of a RFID reader, and a display. The display and identification unit are moveable along the outer edge of the table. Temporary storage positions are provided on the inside of the table, i.e. on the table surface between the guiding groove and the operator. The temporary storage positions are visually indicatable by means of LEDs or the like, similar to the previously discussed embodiment.

During use, the operator moves the tray/container along the guiding groove, together with the identification unit and the display, and places items one after each other on the temporary storage positions, in a similar way as discussed above, and then repeats the movement during packing.

Figure 11:
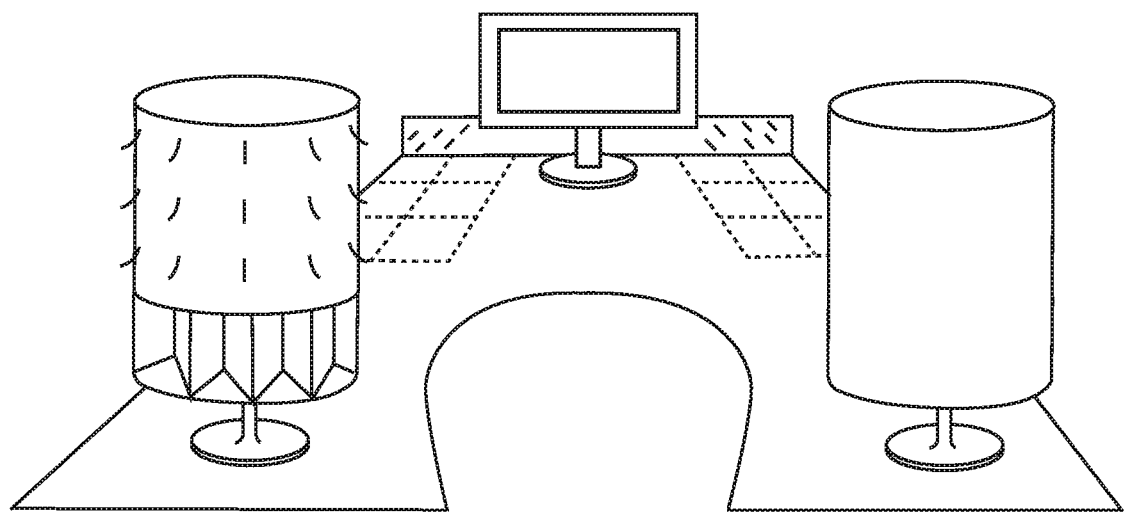

The embodiment illustrated in FIG. 11 is similar to the first discussed embodiment, but here the vertical walls with hangers and shelves have been replaced by hangers and/or shelves arranged on one, two or more rotating cylinders. The cylinders are preferably arranged on one or both sides of the table. The cylinders may be rotated manually. However, preferably the cylinders are electrically operated, and controlled by the controller, so that the cylinders are rotated in accordance with selected temporary storage positions during sorting and packing. This means that the motors turn the cylinders so that the storing position for the chosen item may come as close to the operator as possible. As before, a visual indication is provided for each temporary storage position. Since it might be hard to fit all the different tools using only two cylinders, some additional zones may exist as well, such as a table surface, as in the previously discussed embodiment.

Figure 12:
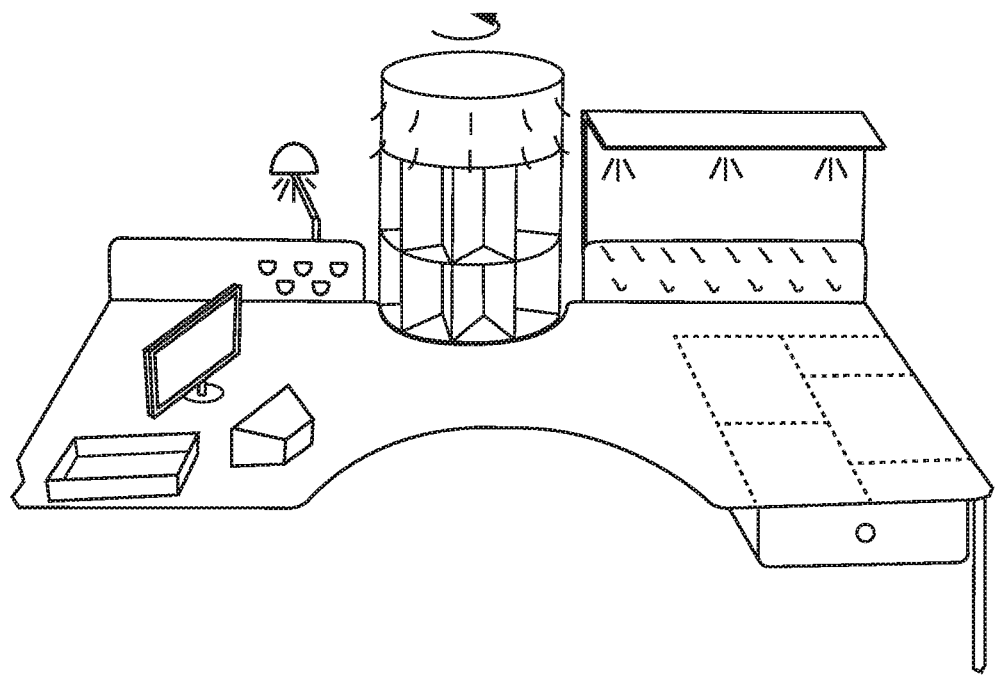

In a further embodiment, illustrated in FIG. 12, a rotating cylinder is again used to provide temporary storage positions, similar to the embodiment of FIG. 11. However, here a single cylinder is used, and is placed centrally on the table. Again, the cylinder may be electrically operated. The cylinder may also be vertically displaceable, so that it may be moved upwards and downwards to make the temporary storage positions easier to access. In addition to the cylinder, additional temporary storage positions may optionally be provided, such as on the table surface and/or on one or several vertical walls. By placing the cylinder in front of the operator a more ergonomic work position is obtained, as well as better possibilities of adding additional storage areas. As in the other embodiments, an identification unit is provided for automated assistance in identifying the items, and visual indications are provided to indicate selected temporary storage positions.

Figure 13:
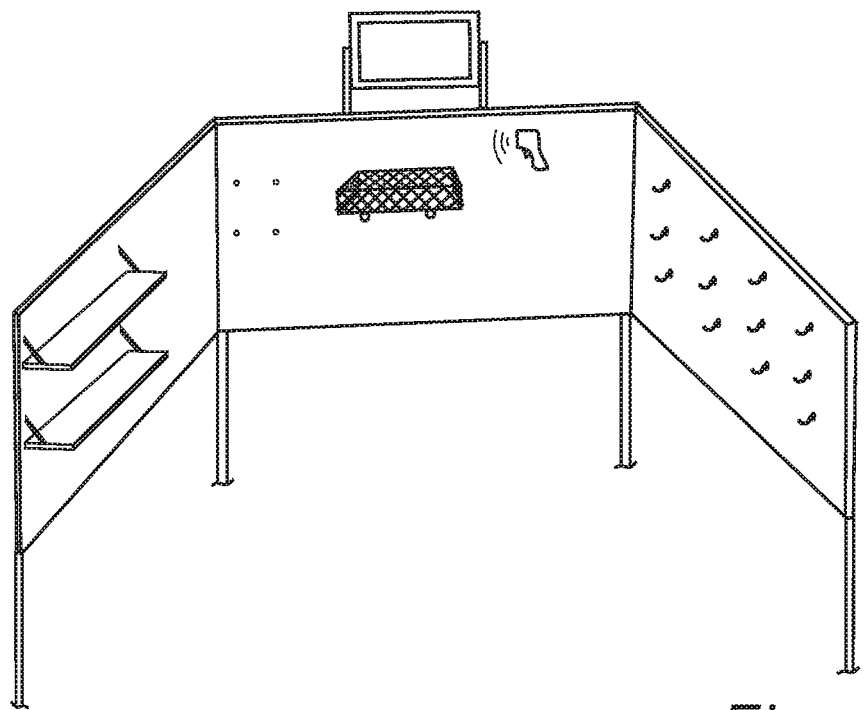

In FIG. 13, a further embodiment is shown. Here, the temporary storage positions are only provided on vertical walls. To this end, the walls may be provided with hangers and/or shelves, or any other suitable mechanism for temporarily holding an item. The walls are arranged in a curved configuration, and e.g. three walls may be used, arranged in a U-formation. Since there is no table surface, this embodiment becomes more compact, thereby minimizing the footprint of the workstation. A display, identification unit etc may be connected to one of the walls, and preferably the central wall. Further, a holding structure may be provided to hold a tray/container, to provide the input and output area. As in the other embodiments, visual indications are provided to indicate selected temporary storage positions.

Figure 14:
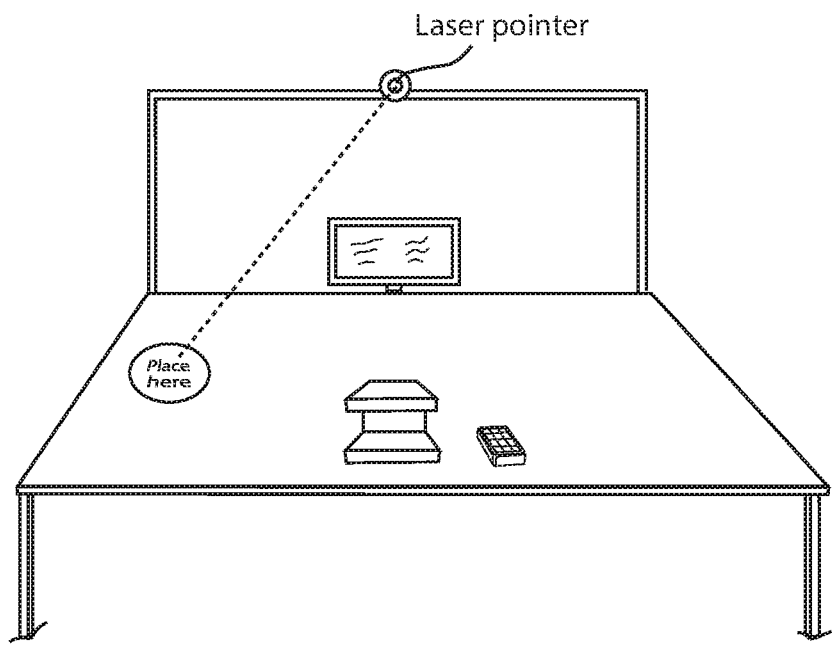

In the embodiment of FIG. 14, an alternative way of providing visual indication of selected temporary storage positions is provided. Similar to some of the previous embodiments, the temporary sorting area here comprises a table surface. Visual indication of selected temporary storing position is provided by a light pointer, such as a laser pointer, which is operable to illuminate various positions on the temporary sorting area. The light pointer is consequently controlled to illuminate the whole or a part of a temporary storage position, indicating where on the table the operator should place a new item, or from where the operator should pick an item for packing. This minimizes the risk of not having any temporary storing position that fits a certain item during sorting. With this system it is also easy to optimize the main surface so that it is used in the most efficient way depending on the incoming items. As in the other embodiments, an identification unit is provided for automated assistance in identifying the items, and visual indications are provided to indicate selected temporary storage positions.

Figure 15:
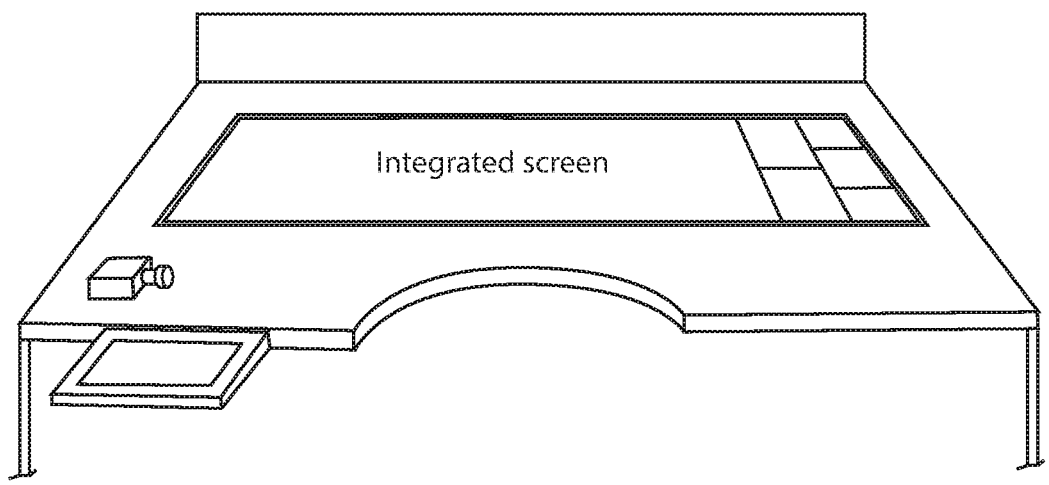

Another way of providing visual indications of temporary storage positions is illustrated in FIG. 15. Here, the table surface comprises an integrated screen. The screen may be used to visually indicated temporary storage positions in various ways, such as showing the frame of the temporary storage position, by flashing light points at the selected position, by showing an image of the object to be placed at the designated position, etc. Thus the display itself is here used to highlight where to place the items and later which item that should be packed. The workstation may also, optionally, comprise a vertical area with hangers and/or shelves, where some items can be placed if necessary. However, alternatively, the temporary sorting area may be formed only by the screen. The screen is preferably relatively large, and may even cover essentially the entire table surface. In this case, the screen may even form the table surface. The screen is preferably a touch screen, thereby also functioning as input interface for the operator, and may also be used to display information etc, as in the previously discussed embodiments. As in the other embodiments, an identification unit is provided for automated assistance in identifying the items, and visual indications are provided to indicate selected temporary storage positions.

The above-discussed embodiments are primarily intended for use as workstations for assembling clean medical instruments and tools coming from a cleaning facility into packed sets to be subsequently sterilized. However, the workstations may also be used for sorting and packing used tools and instruments immediately after operations. The responsible person, typically a nurse, may then put the tray with the used instruments in the input area, identify each object, one at a time, in the same way as discussed above, and place them at dedicated and visually indicated temporary storage positions. Thereafter, the objects are placed back again, following the original set list for the set, and with use of the visual indications as discussed in the foregoing. After completion it is confirmed that all objects belonging to the set are still there, and a confirmation label may optionally be printed. This ensures, in a fast and highly reliable way, that all tools and instruments of a particular set are also returned, ensuring that no object is missing, and in the worst case remains within the patient. The above-discussed embodiments may be used also for this situation. However, for this use, certain parts of the system, such as the additional tables and the drawers, may be omitted, since there is generally no need for additional cleaning, quality inspection and sealing in this situation.

Workstations of this type may also similarly be used in other situations where there is a need to assemble sets of medical tools and instruments, or to repack such tools and instruments to confirm completeness of the set or the like.

Workstations of this type may also be used to assist operators, typically nurses, when assembling customized sets of pharmaceutical products for patients. In particular, it is well suited for administration of pharmaceutical products, such as pills, in administration doses. Hereby, incoming pharmaceutical product containers may be identified by the identification unit, by reading of a bar code, text recognition or the like. The product containers are then placed at dedicated temporary storage positions, such as compartments on shelves, indicated to the operator by the controller by means of the visual indications. When dose sets of products should be assembled, which is typically made one or several times a day, or less frequently, such as every day, every two or three days, or even once or twice a week, the operator selects a patient for which the set is intended in the system. The system then identifies a dose set list, and guides the operator to pick the correct pharmaceutical products and the correct dose of each product, by use of the visual indication system discussed in the foregoing. When a set has been assembled, the operator may print a label to be attached to the container, indicating for which patient it is intended and optionally also when the pharmaceutical products should be administered. The label may also comprise an identity, such as a bar code or the like, which may be read by a bar code scanner or the like during the administration process, to increase quality and security. For example, the identity may be used to confirm when the container is picked from a storage, and when it is administered. Hereby, it is easy to monitor and trace the intake of all pharmaceutical products being administered for each and every patient.

The container may also be a multi-compartment container, having e.g. compartments for specific times of the day, such as a compartment for the morning, a compartment for lunch, a compartment for the afternoon and a compartment for the night. Additionally, or alternatively, the multi-compartment container may have compartment(s) intended for different days.

Use of the workstation for this line of use makes the assembly process quicker and more efficient, and minimizes the risk of errors. The entire process is also traceable and can be verified afterwards, should the need arise.

The above-discussed embodiments may be used also for this situation. However, for this use, certain parts of the system, such as the additional tables and the drawers, may be omitted, since there is generally no need for additional cleaning, quality inspection and sealing in this situation. Further, the temporary storage area may be adapted to accommodate pill containers and the like, whereby shelves and possibly drawers are preferred compared to hangers and table surfaces.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A system for assembling sets of medical instruments, the system comprising:
    a control system comprising or being connected to a database, said database comprising data objects corresponding to available medical instruments;
    an input area, arranged to receive batches of unsorted medical instruments;
    an identification area having an identification unit;
    a temporary sorting area comprising a plurality of storage positions for medical instruments, the storage positions being provided with visual indications capable of visually indicating one of said plurality of storage position at a time; and
    an output area arranged to receive medical instruments as assembled sets;
    wherein the controller is arranged to receive information from the identification unit obtained when a medical instrument is arranged on said identification area, and to identify the medical instruments in said database, to dedicate and visually indicate an empty storage position for said identified medical instrument in said temporary sorting area and to visually indicate occupied storage positions in said temporary sorting area one at a time in accordance with a set order.

2. The system of claim 1, wherein the identification unit comprises an optical identification unit.

3. The system of claim 1, wherein identification of said medical instrument based on recognition of at least one of: a machine readable optical identification, a radio frequency identification (RFID), physical dimensions, physical shape, and weight.

4. The system of claim 1, wherein the temporary sorting area comprises a table surface comprising a plurality of visual indications.

5. The system of claim 4, wherein the table surface with said visual indications comprises a transparent or semi-transparent top cover, and a LED plate formed by a plurality of LED circuit boards beneath said top cover.

6. The system of claim 5, wherein the LED circuit boards have a quadratic or rectangular form, and a break line extending along at least one of the two diagonals.

7. The system of claim 4, wherein the table surface with said visual indications comprises a display.

8. The system of claim 1, wherein the temporary sorting area comprises at least one of: a shelf and hooks, arranged on a supporting structure.

9. The system of claim 1, further comprising a display arranged to display information to the user about at least medical instrument to be picked in accordance with a set order.

10. The system of claim 1, further comprising a confirmation button.

11. The system of claim 1, further comprising a label writer being communicably coupled to said controller.

12. A workplace arrangement comprising a plurality of systems in accordance with claim 1.

13. The workplace arrangement of claim 12, wherein the systems are arranged back-to-back, in a triangular or quadratic configuration.

14. The workplace arrangement of claim 12, further comprising at least one shared resource arranged between the systems.

15. A method for assembling sets of medical instruments the method comprising:
    receiving a batch of unsorted medical instruments;
    automatically identifying with a controller one medical instrument at a time using an identification unit;
    assigning with the controller an empty storage position in a temporary sorting area to the identified medical;
    visually indicating the assigned storage position with the controller;
    acquiring a set order in said controller; and
    visually indicating, with said controller, occupied storage positions in said temporary sorting area one at a time in accordance with the set order.

* * * * *